(12) United States Patent
Rose et al.

(10) Patent No.: US 11,969,274 B2
(45) Date of Patent: Apr. 30, 2024

(54) IMAGING SYSTEMS AND METHODS

(71) Applicant: SIEMENS HEALTHINEERS INTERNATIONAL AG, Steinhausen (CH)

(72) Inventors: Steven Rose, Hausen im Wiesental (DE); Mathias Lehmann, Zurich (CH); Andres Graf, Oberwil (CH)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 0 days.

(21) Appl. No.: 16/368,862

(22) Filed: Mar. 29, 2019

(65) Prior Publication Data
US 2020/0305807 A1   Oct. 1, 2020

(51) Int. Cl.
*A61B 6/04*     (2006.01)
*A61B 6/00*     (2006.01)
*A61B 6/03*     (2006.01)
A61B 6/46      (2024.01)

(52) U.S. Cl.
CPC ............ *A61B 6/0407* (2013.01); *A61B 6/035* (2013.01); *A61B 6/5241* (2013.01); *A61B 6/465* (2013.01); *A61B 6/469* (2013.01); *A61B 2576/00* (2013.01); *G06T 2207/20212* (2013.01); *G06T 2207/30004* (2013.01)

(58) Field of Classification Search
None
See application file for complete search history.

(56) References Cited

U.S. PATENT DOCUMENTS

| | | | | |
|---|---|---|---|---|
| 5,295,200 A * | 3/1994 | Boyer | ..................... | G06K 9/32 |
| | | | | 382/130 |
| 2007/0110289 A1* | 5/2007 | Fu | .......................... | G06V 10/24 |
| | | | | 382/128 |
| 2007/0140427 A1* | 6/2007 | Jensen | .................... | A61B 6/481 |
| | | | | 378/98.12 |
| 2008/0152088 A1* | 6/2008 | Wang | ....................... | H04N 5/32 |
| | | | | 378/98.12 |
| 2010/0195792 A1 | 8/2010 | Kunz et al. | | |
| 2011/0038454 A1* | 2/2011 | Minnigh | ................ | A61B 6/587 |
| | | | | 378/62 |
| 2011/0206185 A1 | 8/2011 | Sakai et al. | | |

(Continued)

OTHER PUBLICATIONS

International Search Report and Written Opinion dated Apr. 28, 2020 for corresponding PCT Application No. PCT/EP2020/057778.

*Primary Examiner* — Edwin C Gunberg
(74) *Attorney, Agent, or Firm* — Duane Morris LLP

(57) ABSTRACT

An image acquisition apparatus includes: a positioner controller communicatively coupled to a positioner, wherein the positioner controller is configured to generate a control signal to cause the positioner to rectilinearly translate a patient support relative to an imager, and/or to rectilinearly translate the imager relative to the patient support; an imaging controller configured to operate the imager to generate a first plurality of two-dimensional images for a patient while the patient is supported by the patient support, and while the positioner rectilinearly translates the patient support and/or the imager; and an image processing unit configured to obtain the first plurality of two-dimensional images and arrange the two-dimensional images relative to each other to obtain a first composite image.

29 Claims, 8 Drawing Sheets

(56) References Cited

U.S. PATENT DOCUMENTS

| | | | |
|---|---|---|---|
| 2013/0064344 A1* | 3/2013 | Carol | A61B 6/5205 |
| | | | 378/10 |
| 2013/0129179 A1* | 5/2013 | Lee | G06T 3/4038 |
| | | | 382/132 |
| 2013/0140467 A1* | 6/2013 | Kitano | H04N 7/18 |
| | | | 250/394 |
| 2014/0093044 A1* | 4/2014 | Behiels | A61B 6/5241 |
| | | | 378/62 |
| 2014/0105357 A1* | 4/2014 | Shin | A61B 6/5241 |
| | | | 378/62 |
| 2014/0254753 A1 | 9/2014 | Yamashita | |
| 2015/0213633 A1 | 7/2015 | Chang et al. | |
| 2016/0310098 A1* | 10/2016 | Kim | A61B 6/5241 |
| 2019/0000564 A1 | 1/2019 | Navab et al. | |

* cited by examiner

| Point / Perspective Projection (regular DRR) | Parallel Projection | 'Focal-Line' Projection |
|---|---|---|
|  |  |  |

IMAGING SYSTEMS AND METHODS

FIELD

The field of the application relates to medical imaging, and more particularly, to systems and methods for imaging a patient before and/or during treatment.

BACKGROUND

Image guidance in radiation therapy is an essential tool to provide high quality treatments by aligning the patient's current anatomy with a planned configuration. The field of view of existing imaging modalities (e.g., 2D planar, CBCT imaging, etc.) may be restricted by the size of the image receptor to about 30 cm or less in length at isocenter level. To be able to treat longer patient volumes, image guidance needs to provide a longer field of view to provide sufficient confidence in the patient's alignment with respect to planned configuration. In some cases, the longitudinal field of view of CBCT may be extended by combining separate CBCT scan acquisitions from different couch positions. However, this approach may not be desirable because of its long acquisition time and because it results in high amount of non-treatment radiation dose being delivered to the patient.

SUMMARY

An image acquisition apparatus includes: a positioner controller communicatively coupled to a positioner, wherein the positioner controller is configured to generate a control signal to cause the positioner to rectilinearly translate a patient support relative to an imager, and/or to rectilinearly translate the imager relative to the patient support; an imaging controller configured to operate the imager to generate a first plurality of two-dimensional images for a patient while the patient is supported by the patient support, and while the positioner rectilinearly translates the patient support and/or the imager; and an image processing unit configured to obtain the first plurality of two-dimensional images and arrange the two-dimensional images relative to each other to obtain a first composite image.

An imaging method performed by an image acquisition apparatus, includes: generating a control signal by a positioner controller that is communicatively coupled to a positioner, wherein the control signal is generated to cause the positioner to rectilinearly translate a patient support relative to an imager, and/or to rectilinearly translate the imager relative to the patient support; operating the imager to generate a first plurality of two-dimensional images for a patient while the patient is supported by the patient support, and while the positioner rectilinearly translates the patient support and/or the imager; and arranging, by an image processing unit, the two-dimensional images relative to each other to obtain a first composite image.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
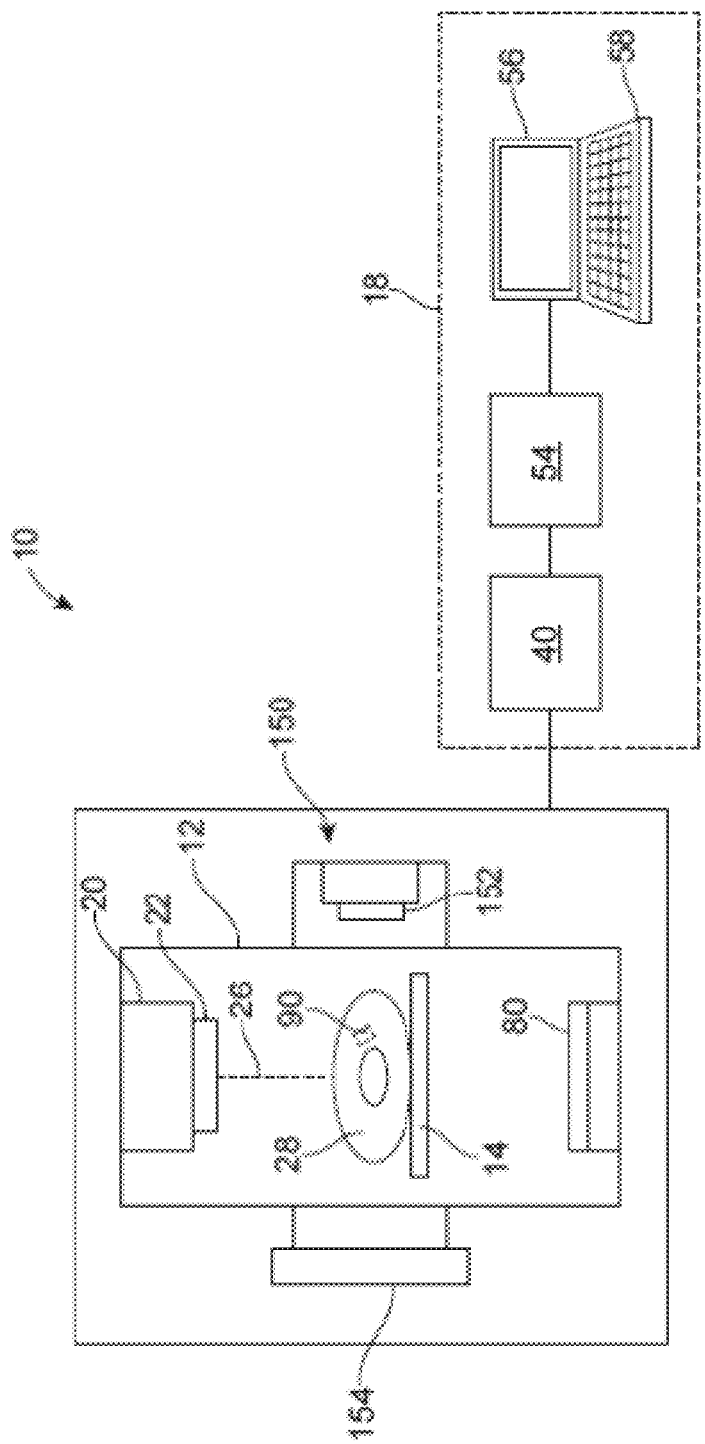
FIG. 1 illustrates a radiation system having an imager in accordance with some embodiments.

Various embodiments are described hereinafter with reference to the figures. It should be noted that the figures are not drawn to scale and that elements of similar structures or functions are represented by the same reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a treatment system 10. The system 10 is a radiation treatment system that includes a gantry 12, a patient support 14 for supporting a patient 28, and a control system 18 for controlling an operation of the gantry 12. The gantry 12 is in a form of an arm, but in other embodiments, the gantry 12 may have other forms (such as a ring form, etc.). The system 10 also includes a radiation source 20 that projects a beam 26 of radiation towards a patient 28 while the patient 28 is supported on support 14, and a collimator system 22 for controlling a delivery of the radiation beam 26. The collimator 22 may be configured to adjust a cross sectional shape of the beam 26. The radiation source 20 can be configured to generate a cone beam, a fan beam, or other types of radiation beams in different embodiments.

As shown in the figure, the system 10 also includes an imager 80, located at an operative position relative to the source 20 (e.g., under the support 14). In the illustrated embodiments, the radiation source 20 is a treatment radiation source for providing treatment energy. In such cases, the treatment energy may be used by the imager 80 to obtain images. In order to obtain imaging using treatment energies, the imager 80 is configured to generate images in response to radiation having treatment energies (e.g., MV imager). In other embodiments, in addition to being a treatment radiation source, the radiation source 20 can also be a diagnostic radiation source for providing diagnostic (imaging) energy for imaging purpose. In further embodiments, the system 10 may include the radiation source 20 for providing treatment energy, and one or more other radiation sources for providing diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. Also, in some embodiments, a treatment energy may be 6 MV or higher (e.g., 25 MV). In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In other embodiments, the radiation source 20 may be configured to generate radiation at other energy ranges, such as a range that is below 160 keV, a range from 1 MeV to 12 MeV or less, etc.

In the illustrated embodiments, the control system 18 includes a processing unit 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processing unit 54. In some cases, the control 40 may also control the collimator system 22 and the position of the patient support 14. In addition, in some embodiments, the control 40 may be configured to control an operation of the imager 80. Although the control 40 is shown as a separate component from the gantry 12 and the processor 54, in alternative embodiments, the control 40 can be a part of the gantry 12 or the processing unit 54.

In some embodiments, the system 10 may be a treatment system configured to deliver a treatment radiation beam towards the patient 28 at different gantry angles. During a treatment procedure, the source 20 rotates around the patient 28 and delivers a treatment radiation beam from different gantry angles towards the patient 28. While the source 20 is at different gantry angles, the collimator 22 is operated to change the shape of the beam to correspond with a shape of the target tissue structure. For example, the collimator 22 may be operated so that the shape of the beam is similar to a cross sectional shape of the target tissue structure. In another example, the collimator 22 may be operated so that different portions of the target tissue structure receive different amount of radiation (as in an IMRT procedure).

In the illustrated embodiments, the system 10 also includes an imaging device 150 having an imaging source 152 and an imager 154. The imaging device 150 is configured to obtain one or more images of an internal part of the patient 28. The image(s) obtained by the imaging device 150 may be used to setup the patient 28, monitor a position of the patient 28, track a target within the patient 28, or any combination of the foregoing. In some cases, the imaging device 150 may be configured to obtain images of an internal fiducial 90 of the patient 28. The internal fiducial 90 may be an internal structure inside the patient 28. In some embodiments, the internal structure may move in correspondence (e.g., in sync) with a target of the patient 28 that is desired to be treated. In such cases, the internal structure may be used as a surrogate for determining a position and/or movement of the target during treatment of the patient 28, and motion management based on the surrogate may be employed in some cases. Thus, the internal fiducial 90 may be imaged by the imaging device 150 (and/or by the radiation source 20 and imager 80) that functions as a position monitoring system during a treatment of the patient 28. By means of non-limiting examples, the internal fiducial 90 may be an anatomical surrogate, such as bony structure, a vessel, a natural calcification, or any other items in a body. As discussed, the imaging device 150 and/or the imager 80 may also be used for target tracking and/or patient positioning. In some embodiments, the control 40 may be configured to control an operation of the imaging device 150 and/or the patient support 14. For example, the control 40 may provide one or more control signals to activate the imaging source 152, and/or to operate a readout and control circuit in the imager 154. The control 40 may also operate a positioner to move the patient support 14 and/or the imaging device 150.

In some embodiments, the imaging device 150 may be a x-ray device. In such cases, the imaging source 152 comprises a radiation source (e.g, a kV source). In other embodiments, the imaging device 150 may have other configurations, and may be configured to generate images using other imaging techniques. For example, in other embodiments, the imaging device 150 may be an ultrasound imaging device, a MRI device, a tomosynthesis imaging device, or any of other types of imaging devices. Also, in the above embodiments, the imaging device 150 is illustrated as being integrated with the treatment machine. In other embodiments, the imaging device 150 may be a separate device that is separate from the treatment machine. In addition, in some embodiments, the imaging device 150 may be a room-based imaging system or a couch based imaging system. In either case, the imaging device 150 may provide any form of imaging, such as x-ray imaging, ultrasound imaging, MRI, etc. Furthermore, in other embodiments, the imaging device 150 may provide in-line imaging in the sense that it may be configured to acquire images along the same direction as the treatment beam. For example, a dual-energy source (integrating the treatment source 20 and the imaging source 152) may be provided to provide imaging energy for generating an image, and to provide treatment energy to treat a patient along the same direction. In such cases, the imager 154 may replace the imager 80, or may be integrated with the imager 80 to form a hybrid-imager, which is configured to provide kV and MV imaging. In still further embodiments, the imaging device 150 and/or the imaging device 80 may be configured to provide dual energy imaging and any form of energy-resolved imaging to increase contrast in x-ray images. For example, a first part of an image may be generated using a first energy, and a second part (e.g., a more relevant part that includes a target) of the same image may be generated using a second energy that is higher than the first energy. As a result, the second part of the image may have higher contrast compared to the first part. However, the overall dose involved in generating the whole image may be reduced compared to the situation in which the entire image is generated using the second energy.

Figure 2:
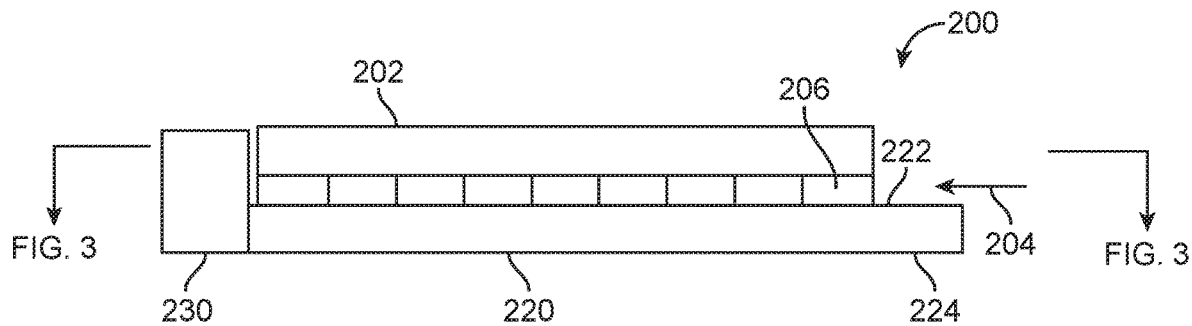
FIG. 2 illustrates an imager.

FIG. 2 illustrates an example of an imager 200. The imager 200 may implement as the imager 154 or the imager 80 of FIG. 1 in some embodiments. The imager 200 is configured to receive imaging radiation from an imaging source (e.g., source 152 or 20), and generates image signals in response to the imaging radiation. The imager 200 includes a layer 202 of scintillator (or scintillator layer 202) configured to receive the imaging radiation, and to generate light in response to the imaging radiation. The scintillator layer 202 may be pixelated or non-pixelated. The imager 200 also includes an array 204 of imager elements 206. Each imager element 206 is configured to generate image signal(s) in response to light received from the scintillator layer 202. Scintillators for imagers are known in the art, and any of such scintillators may be used to implement the imager 200.

In some embodiments, each imager element 206 may include one or more amorphous silicon (a:Si) detector. Also, in some embodiments, the imager element 206 may be implemented using a photodiode. In this specification, the term "photodiode" refers to one or more electrical circuit element(s) on a detector pixel that are associated with converting photon energy into electrical signals. This can include, but is not limited to, photodiode(s), switching transistor(s), amplification transistor(s), direct conversion element, indirect conversion elements, photon counting elements, or a combination thereof. In some embodiments, the electrical circuit element(s) of the imager element 206 is designed (e.g., being made from radiation resistant material, and/or having a configuration) to be radiation hard. The scintillator layer 202 is configured to receive radiation and generate photons in response to the radiation. The photodiode element of the imager element 206 is configured to generate electrical signals in response to the photons provided from the scintillator layer 202. The electrical signals are then read out by readout and control circuit 230, and are digitized to form an image. In the illustrated embodiments, the readout and control circuit 230 is designed (e.g., being made from radiation resistant material, and/or having a configuration) to be radiation hard. In some embodiments, the readout and control circuit 230 is communicatively connected to the control 40, or another separate control, for controlling an operation of the readout and control circuit 230.

In some embodiments, signal from each photodiode of each imager element 206 forms a pixel in an image. In other embodiments, a binning circuit is optionally provided to combine the signals from two or more photodiodes of two or more respective imager elements 206 to form each pixel in the image. For example, the binning circuit of the imager 200 may be configured to provide 2×2 binning, 3×3 binning, 4×4 binning, 1×2 binning, 1×4 binning or binning of other number of pixels. In some embodiments, the binning circuit may be designed (e.g., being made from radiation resistant material, and/or having a configuration) to be radiation hard. For example, the binning circuit may include circuit components configured to withstand radiation. The binning circuit may be implemented as a part of the access and control circuit 230 in some embodiments.

As shown in FIG. 2, the imager 200 further includes a glass substrate 220, wherein the array 204 of imager elements 206 is secured to the glass substrate 220. In the illustrated embodiments, the glass substrate 220 has a first side 222 and an opposite second side 224, wherein the first side 222 is closer to a radiation source than the second side 224. In some embodiments, the array 204 of imager elements 206 is located closer to the first side 222 of the glass substrate 220 than the second side 224. In other embodiments, the substrate 220 may be made from other materials that are different from glass. For example, in other embodiments, the substrate 220 may be made from plastic.

Figure 3:
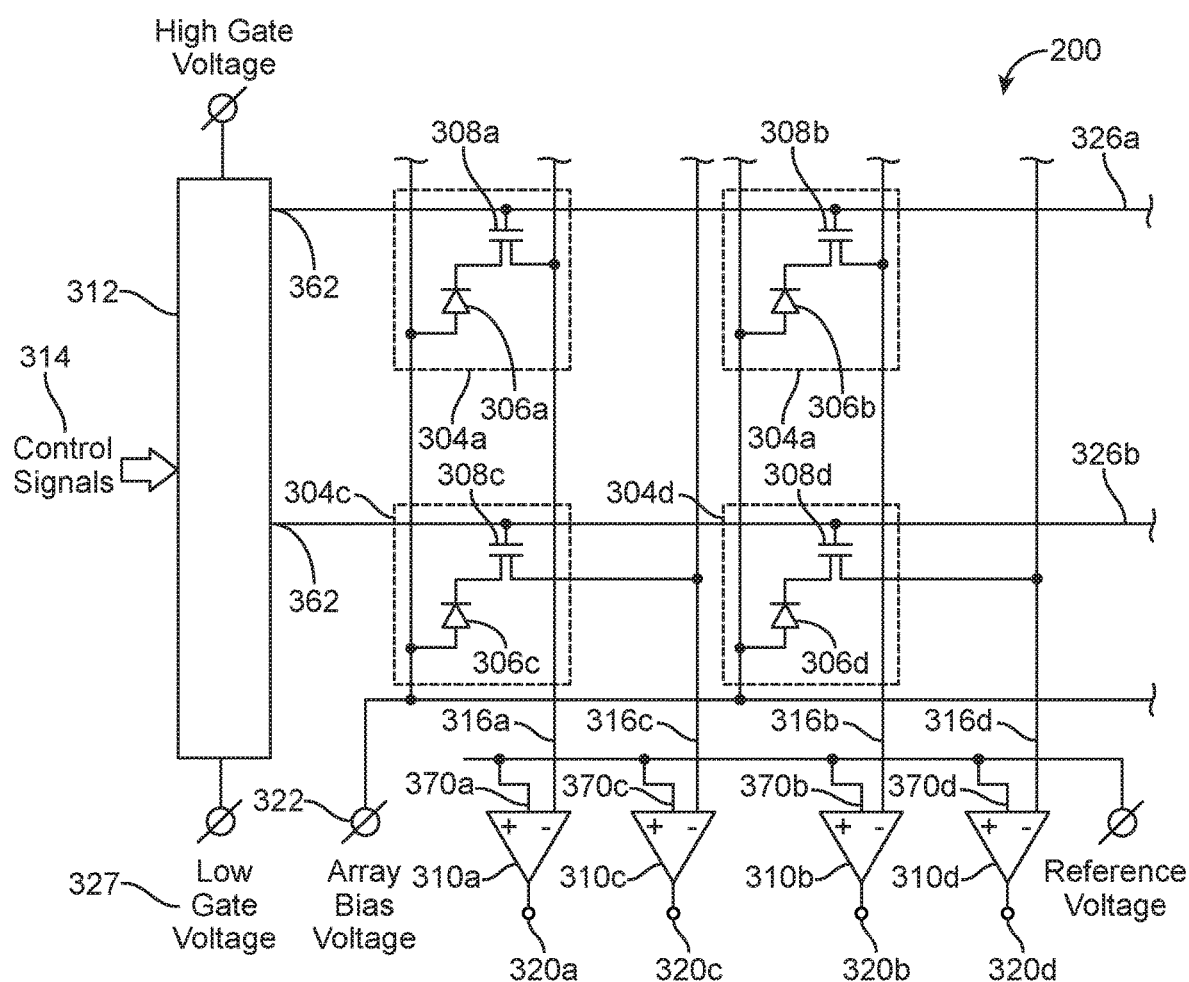
FIG. 3 illustrates exemplary electrical components of the imager of FIG. 2.

FIG. 3 depicts one exemplary configuration of electrical components for the imager 200 in accordance with some embodiments. The imager 200 includes a plurality of imager elements 304 (i.e., 304a-304d) having respective photodiodes 306 (i.e., 306a-306d). The photodiodes 306 form part of the imager element 206 of FIG. 2. Each of the photodiodes 306 is configured to generate an electrical signal in response to a light input. The photodiode 306 receives light input from the scintillator layer 202 that generates light in response to x-rays. The photodiodes 306 are connected to an array bias voltage 322 to supply a reverse bias voltage for the imager elements 304. A transistor 308 (such as a thin-film N-type FET) functions as a switching element for each imager element 304. When it is desired to capture image data from the imager elements 304, control signals 314 are sent to a gate driver 312 to "select" the gate(s) of transistors 308. The gate driver 312 is connected to a low gate voltage 327 and high gate voltage source that drives the gate control lines 326a, 326b. In particular, the gate driver 312 provides drive signals to the gate control lines 326a, 326b. In response to the drive signals, electrical signals from the photodiodes 306 are passed through lines 316 (i.e., 316a-316d) to corresponding charge amplifiers 310a-310d, which are connected to a reference voltage via lines 370a-370d, respectively. The output of the charge amplifiers 310 is sent via outputs 320 (e.g., 320a-320d) to a "sample and hold" stage for further image processing/display. In one embodiment, the gate driver 312 is a part of the readout and control circuit 230 of FIG. 2, which may be located along one or more side(s) of the imager 200. The readout and control circuit 230 may include one or more of the components shown in FIG. 3, such as the gate driver 312, the charge amplifiers 310, the outputs 320, gate control lines 326, lines 316, lines 370, reference voltage source and/or conductor of the reference voltage, array bias voltage and/or conductor of the array bias voltage, high and low gates voltage source and/or conductor of the high and low gates voltage, the digital control circuits, or any combination of the foregoing. In some embodiments, one or more (e.g., all) of the above components of the readout and control circuit 230 may be radiation hard. In addition, in some embodiments, the readout and control circuit 230 may be a part of an integrated circuit, wherein a part or an entirety of the integrated circuit may be radiation hard. Such circuit may include any of the components of the readout and control circuit 230 described above, including but not limited to gate driver 312, charge amplifiers 310, digital control circuits, etc.

While FIG. 3 only shows four imager elements 304a-304d, those skilled in the art understand that the imager 200 may include many such imager elements 304, depending upon the size and resolution of the imaging device. In addition, although only two gate control lines 326a and 326b for accessing image signals from imager elements 304 are shown, the imager 200 may include more than two gate control lines 326. In the illustrated embodiments, the gate driver 312 has multiple outputs 362 accessing respective gate control lines 326, one line at a time. In other embodiments, the gate driver 312 may be configured to access multiple (e.g., two, four, six, etc.) gate control lines 326 simultaneously. For example, each output 362 of the gate driver 312 may connect to multiple gate control lines 326 for accessing the multiple gate control lines 326 simultaneously. Such configuration allows image signals to be collected from two or more lines of imager elements 304 simultaneously, thereby increasing the signal collection process. For a given configuration of the imager 200, a signal readout time for each gate control line 326 of imager elements 304 depends on the time it takes to turn on a pixel and discharge a corresponding image signal. As such, by configuring the imager 200 to allow image signals from two or more lines of imager elements 304 to be read simultaneously or in parallel, the time it takes to readout image signals from all the lines of the imager 200 can be reduced. This in turn, improves the frame rate (i.e., number of image frames that can be generated by the imager 200 per second) of the imager 200.

It should be noted that the electrical components and the electrical layout of the imager 200 should not be limited by the example shown in FIG. 3, and that in other embodiments, the imager 200 may have electrical component(s) and/or electrical layout that is different from that shown in FIG. 3.

It should be noted that the imager 200 described herein is not limited to withstand radiation resulted from treatment beam generated by electrons striking a target. In other embodiments, the imager 200 described herein may be for withstanding radiation resulted from other types of particle beams, such as proton beams. For example, the imager 200 described herein may be used with a proton treatment machine. In such cases, the features described herein may allow the imager 200 to withstand radiation resulted from the delivery of proton treatment beam.

Furthermore, the imager 200 is not limited to having the scintillator layer 202. In other embodiments, the imager 200 may be other types of imager, such as those that may not require any scintillator layer. For example, as discussed, in other embodiments, the imager 200 may include a conversion layer that is configured to generate electron-hole pairs in response to radiation. In such cases, image signals are generated directly by the conversion layer, and the imager 200 may not include any scintillator layer. Also as similarly discussed, in further embodiments, the imager 200 may include photon counters configured to generate image(s) based on photon counting. Imagers with conversion layers and photon counters are known in the art, and any of such imagers may be used to implement the imager 200. The imager 200 may be any other type of imager in other embodiments.

Imagers in radiation therapy systems and in diagnostic radiation system are well known in the art, and any of such imagers may be used to implement the imager 200.

Figure 4:
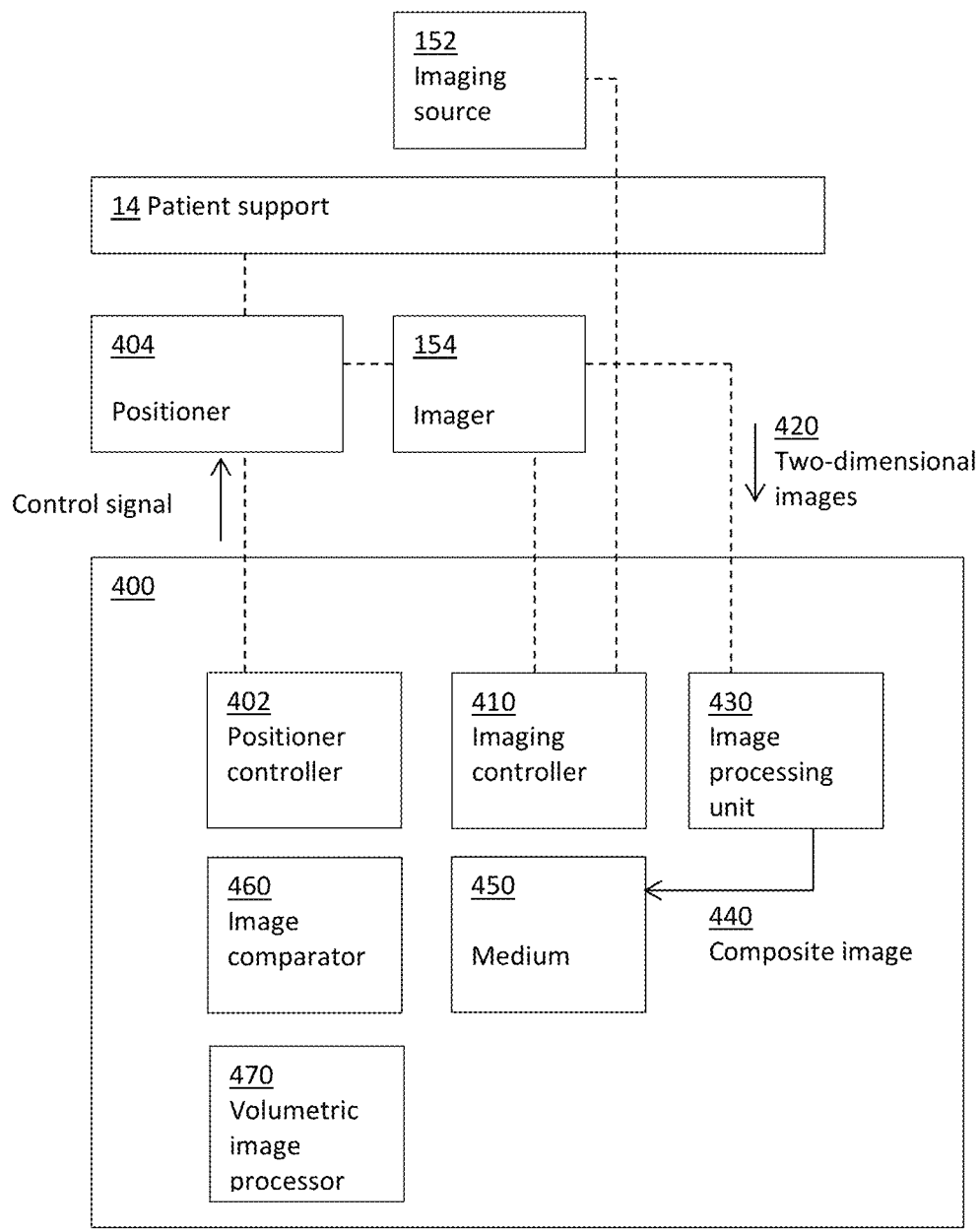
FIG. 4 illustrates an image acquisition apparatus.

FIG. 4 illustrates an image acquisition apparatus 400 in accordance with some embodiments. The image acquisition apparatus 400 may be implemented in the treatment system 10 of FIG. 1. For example, the image acquisition apparatus 400 may be implemented as a part of the processing unit 54, or as a separate component that is communicatively coupled to the processing unit 54 and/or the control 40. The image acquisition apparatus 400 includes: a positioner controller 402 communicatively coupled to a positioner 404, wherein the positioner controller 402 is configured to generate a control signal to cause the positioner 404 to rectilinearly translate the patient support 14 relative to the imager 154 and the imaging source 152, and/or to rectilinearly translate the imager 154 and the imaging source 152 relative to the patient support 14. The image acquisition apparatus 400 also includes an imaging controller 410 configured to operate the imager 154 to generate a first plurality of two-dimensional images 420 for a patient while the patient is supported by the patient support 14. The image acquisition apparatus 400 further includes an image processing unit 430 configured to obtain the first plurality of two-dimensional images 420 and arrange the two-dimensional images 420 relative to each other to obtain a first composite image 440.

In some embodiments, the positioner controller 402 is configured to operate the positioner 404 to rectilinearly translate the patient support 14 or the imaging device 150 in a direction that corresponds with (e.g., parallel to) a longitudinal axis of the patient 28. In one implementation, as the patient support 14 is being rectilinearly translated, the imaging device 150 remains stationary (e.g., the imaging source 152 and the imager 154 does not rotate nor translate). In another implementation, as the imaging device 150 is being rectilinearly translated, the patient support 14 remains stationary. In a further implementation, the patient support 14 and the imaging device 150 may be rectilinearly translated in opposite directions. In some cases, the positioner controller 402 is configured to generate the control signal to cause the positioner 404 to translate the patient support 14 at a rate that is at least 80% of the maximum speed of the patient support 14, and/or the imaging device 150 at a rate that is at least 80% of the maximum speed of the imaging device 150. This allows different parts of the patient supported by the patient support 14 to be imaged by the imaging device 150 quickly. In other embodiments, the positioner 404 may translate the patient support 14 at other speeds, which may be below 80% of the maximum speed of the patient support 14. Also, in other embodiments, the positioner 404 may translate the imaging device 150 at other speeds, which may be below 80% of the maximum speed of the imaging device 150.

The positioner controller 402 may also operate the positioner 404 to rotate the imaging device 150 (the imaging source 152 and the imager 154) around the patient so that the imaging device 150 can image the patient from a different angle. As used in this specification, the term "positioner" may refer to one or more mechanical movers. For example, the positioner 404 may be a first mechanical component attached to the patient support 14 for moving the patient support, may be a second mechanical component attached to the imaging device 150 for moving the imaging device 150 or part(s) thereof, or may be both the first and second mechanical components.

The imaging controller 410 is configured to operate the imaging source 152 and/or the imager 154 to generate two-dimensional images 420 for a patient while the patient is supported by the patient support 14. The imaging controller 410 may communicatively couple to readout and control circuit (e.g., readout and control circuit 230) of the imager 154. The imaging controller 410 may also communicatively couple to the imaging source 152. In some embodiments, as the positioner 404 rectilinearly translates the patient support 14 relative to the imaging source 152 and the imager 154, the imaging controller 410 generates signals to operate the imaging source 152 and the imager 154 to image different parts of the patient along a longitudinal axis of the patient. In other embodiments, as the positioner 404 rectilinearly translates the imaging source 152 and the imager 154 relative to the patient support 14, the imaging controller 410 generates signals to operate the imaging source 152 and the imager 154 to image different parts of the patient along a longitudinal axis of the patient. In either case, the imaging of the patient results in multiple two-dimensional images of different parts of the patient that are along a longitudinal axis of the patient. The imaging planes of the respective two-dimensional images are parallel with respect to each other and all lie within the same plane. This allows the image processing unit 430 to stitch the two-dimensional images together in some embodiments to form the composite image 440.

In some embodiments, the imaging controller 410 is configured to operate the imager 154 to generate the plurality of two-dimensional images 420 within 20 seconds or less. Accordingly, the patient only needs to be imaged for 20 seconds or less, and the image acquisition apparatus 400 will have sufficient image data to create the composite image 440 for the patient. Due to the advantage of such short imaging time, the patient may be instructed to perform breath hold while the imager 154 generates the two-dimensional images 420. Also, in some embodiments, the two-dimensional images 420 that are generated within 20 seconds or less (e.g., within 15 seconds, within 12 seconds, within 10 seconds, etc.) collectively cover a length of the patient that is at least 50 cm or more, 60 cm or more, 70 cm or more, 80 cm or more, 90 cm or more, or 100 cm or more. In some embodiments, the first plurality of two-dimensional images 420 comprises at least 50 images, at least 60 images, at least 70 images, at least 80 images, at least 90 images, at least 100 images, or more. Furthermore, in some embodiments, the imaging controller 410 is configured to operate the imager 154 to generate the first plurality of two-dimensional images 420 at 10 frames per second or higher, 20 frames/sec or higher, 30 frames/sec or higher, or 40 frames/sec or higher.

In some embodiments, the image acquisition apparatus 400 may be configured to operate the imager 154 in a full resolution imaging mode (i.e., no binning of image data). In such cases, the imager 154 is operated at a first frame rate (e.g., 10 frames/second) that is less than a maximum frame rate. In such example, the patient travel distance per frame may be 1 cm/frame for example. In other embodiments, the image acquisition apparatus 400 may be configured to operate the imager 154 in reduced longitudinal resolution (e.g., 1×4 binning). This may allow higher readout mode to be implemented. In some cases, a shorter travel distance of 0.33 cm/frame can be achieved with a higher frame rate (e.g., 30 frames/second). In further embodiments, the imaging acquisition apparatus 400 may operate the imager 154 in full resolution imaging mode for this higher frame rate.

Also, in the illustrated embodiments, the imaging controller 410 is configured to control the imaging source 152 to deliver imaging energy (e.g., radiation) in pulses. In some cases, the imaging source 152 may deliver imaging energy in pulses that are synchronized to the imager's 154 frame rate. In other embodiments, the imaging controller 410 is also configured to control the imaging source 152 to deliver imaging energy (e.g., radiation) continuously—e.g., for at least 2 seconds, at least 4 seconds, at least 5 seconds, or at least 6 seconds. While the imaging source 152 is "on" continuously, the patient support 14 is translated relative to the imaging source 152 and the imager 154 to allow the imager 154 to image different parts of the patient. Alternatively, while the imaging source 152 is "on" continuously, the imaging source 152 and the imager 154 are translated relative to the patient support 14 to allow the imager 154 to image different parts of the patient. In further embodiments, the imaging source 152 may be selectively operated in a pulse mode (in which imaging energy is delivered in pulses) or a continuous mode (in which imaging energy is delivered continuously).

The image processing unit 430 is configured to obtain the plurality of two-dimensional images 420 and arrange the two-dimensional images 420 relative to each other to obtain a first composite image 440. In some embodiments, the image processing unit 430 is configured to obtain the composite image 440 by performing image stitching using the two-dimensional images 420. In one implementation, the image processing unit 430 is configured to identify overlapping regions of at least two adjacent two-dimensional images 420. In such cases, the stitching of the two adjacent two-dimensional images 420 may be performed based on the identified overlapping regions. Also in some embodiments, the image processing unit 430 is configured to obtain couch positions for the patient support 14 or imager positions for the imager 154, and utilize the couch positions and/or the imager positions to arrange the two-dimensional images 420 with respect to a reference coordinate for the composite image 440 to be formed. As used in this specification, the term "couch position" refers to a position of a patient support (e.g., bed) that is for supporting a patient, wherein the position may be a location and/or an orientation of the patient support. The image processing unit 430 may also be configured to obtain meta data for the respective two-dimensional images 420, and utilize the meta data to map the two-dimensional images 420 to the reference coordinate for the composite image 440 to be formed. By means of non-limiting examples, the meta data may be positions of the imager 154 that correspond with the respective two-dimensional images 420, positions of the patient support 14 that correspond with the respective two-dimensional images 420, relative positions between the patient support 14 and the imager 154 that correspond with the respective two-dimensional images 420, time stamps of the respective two-dimensional images 420 indicating when they are generated, or any combination of the foregoing. In some embodiments, the composite image 440 created from the two-dimensional images 420 may cover (span) at least a portion of the patient that is at least 50 cm or more, 60 cm or more, 70 cm or more, 80 cm or more, 90 cm or more, or 100 cm or more, in length.

In some embodiments, an arbitrary reference couch position may be specified. In such cases, all metadata of the acquired two-dimensional images 420 may be set with respect to the specified reference couch position. For example, for each acquired two-dimensional image 420, the imager position of the imager 154 relative to the reference couch position at the time of acquisition may be used to determine the relative position of the two-dimensional image 420 with respect to the reference couch position. In other embodiments, instead of a reference couch position, any arbitrary reference position or reference coordinate frame may be set. In such cases, the positions of the two-dimensional images 420 may be determined with respect to such arbitrary reference position or reference coordinate frame. In some embodiments, the positions of the two-dimensional images 420 may be used to stitch the two-dimensional images 420 to create the composite image 440. In other embodiments, the determining of the positions of the two-dimensional images 420 itself may be considered a stitching of the two-dimensional images 420. In some embodiments, the reference coordinate frame may have a width and height defined for the composite image 440 to be formed, wherein such width and height are selected to span the maximum extent of all acquired two-dimensional images 420. Image information for each two-dimensional image 420 is copied or placed into the reference coordinate frame at its corresponding relative position within the reference coordinate frame. Redundant image information in the overlap areas between adjacent images 420 may be combined to produce a continuous image.

In some embodiments, the composite image 440 may comprise a left or right side view of the patient. In other embodiments, the composite image 440 may comprise a top or bottom view of the patient. In further embodiments, the image acquisition apparatus 400 may be configured to create two or more composite images 440. For example, the image acquisition apparatus 400 may operate the positioner 404 to place the imaging device 150 at a first orientation with respect to the patient to image from a left or right side of the patient. The image acquisition apparatus 400 may then operate the imaging device 150 to create a first plurality of two-dimensional images having side views of the patient. The image processing unit 430 then creates a first composite image 440 based on the first plurality of two-dimensional images. For example, the image processing unit 430 may arrange the two-dimensional images 420 in the first plurality of two-dimensional images 420 relative to each other to obtain the first composite image 440. The image acquisition apparatus 400 may then operate the positioner 404 to place the imaging device 150 at a second orientation with respect to the patient to image from a top or bottom side of the patient. The image acquisition apparatus 400 may then operate the imaging device 150 to create a second plurality of two-dimensional images having top or bottom views of the patient. The image processing unit 430 then creates a second composite image 440 based on the second plurality of two-dimensional images. For example, the image processing unit 430 may arrange the two-dimensional images 420 in the second plurality of two-dimensional images 420 relative to each other to obtain the second composite image 440.

In some cases, the plurality of two-dimensional images 420 is obtained at a same isocenter position associated with a treatment machine, such as that shown in FIG. 1. This is advantageous in that bending of the patient support due to weight of the patient may not need to be accounted for.

Also, in some embodiments, the image acquisition apparatus 400 may implement an imager readout mode that allows readout of regions-of-interest (ROIs) with reduced height to achieve a higher frame rate (e.g., 30 fps) at native pixel size resolution. This technique may reduce or eliminate merge artifacts. In one implementation, the imaging source 152 may be vertically collimated to provide only a strip of imaging radiation with reduced height that corresponds with a desired height of a region-of-interest (ROI). This has the benefit of reducing dose delivered to the patient. Also, in some embodiments, information from overlapping scans may be utilized to reduce noise and/or to increase spatial resolution, in order to improve image quality. In further embodiments, auto-exposure mechanism may be employed to improve or optimize image contrast and/or to reduce excessive dose.

As shown in FIG. 4, the image acquisition apparatus 400 includes a non-transitory medium 450 for storing the composite image(s) 440. The non-transitory medium 450 may also store different sets of the two-dimensional images 420 that correspond with the respective composite images 440. In some embodiments, the two-dimensional images 420 may be stored in the non-transitory medium 450 in association with their respective meta data, such as time stamps indicating when the images 420 were created, positions of the imager 154 and/or the patient support 14 when the respective images 420 were created, etc. The non-transitory medium 450 may include one or more storage device(s), and is not limited to a single storage device. In some embodiments, the two-dimensional images 420 and/or the composite image(s) 440 may also be outputted by the image acquisition apparatus 400 for display and presentation to a user.

After the composite image(s) 440 have been generated by the image processing unit 430, the composite image(s) 440 may be utilized for various purposes. In some embodiments, the composite image(s) 440 may be used to align the patient with respect to the treatment system 10. In one implementation, the alignment of the patient with respect to the treatment system 10 may be performed based on a comparison of at least a part of the composite image 440 with at least a part of a reference image. As used in this specification, the term "reference image" refers to any image that is generated ahead of time for use as a reference (e.g., for comparison with another later generated image, for processing with a later generated image, etc.). The reference image may be a CT image, a section of a CT image, an x-ray image, or any other types of image that was generated during treatment planning. The reference image is registered with the treatment plan and it indicates a desired positioning of the patient with respect to a treatment scheme. As shown in FIG. 4, the image acquisition apparatus 400 also includes an image comparator 460 configured to compare at least a part of the composite image 440 with at least a part of a reference image to align the at least a part of the composite image 440 with the at least a part of the reference image. In some embodiments, the positioner controller 402 is configured to move the patient support 14 to place the patient at a desired position with respect to the treatment system 10 based on an alignment between at least a part of the composite image 440 and the at least a part of the reference image.

The composite image(s) 440 may also be used to form volumetric image(s) in some embodiments. As shown in FIG. 4, the image acquisition apparatus 400 further includes a volumetric image processor 470 configured to construct a volumetric image based on the composite image 440. For example, in some embodiments, the composite image 440 may contain information (e.g., geometry of anatomy, including sizes and shapes of various anatomical structures in the patient, etc.) that is useful in the generation of the volumetric image. In such cases, the volumetric image processor 470 will obtain the composite image 440 (either from the image processing unit 430 or from the medium 450), and consider the information in the composite image 440 in the construction of the volumetric image. The volumetric image generated by the volumetric image processor 470 based on the plurality of two-dimensional images 420 may be a CT image or a tomosynthesis image.

Also, in some embodiments, the composite image(s) 440 may be used as prior information for generation of a stitched cone beam computed tomography (CBCT) image. For example, the volumetric image processor 470 may be configured to use the composite image 440 as a map for stitching different CBCT images together to form a composite CBCT image (e.g., super-CBCT image). Techniques for stitching CBCT images are known in the art, and therefore will not be described in further detail herein.

Figure 5:
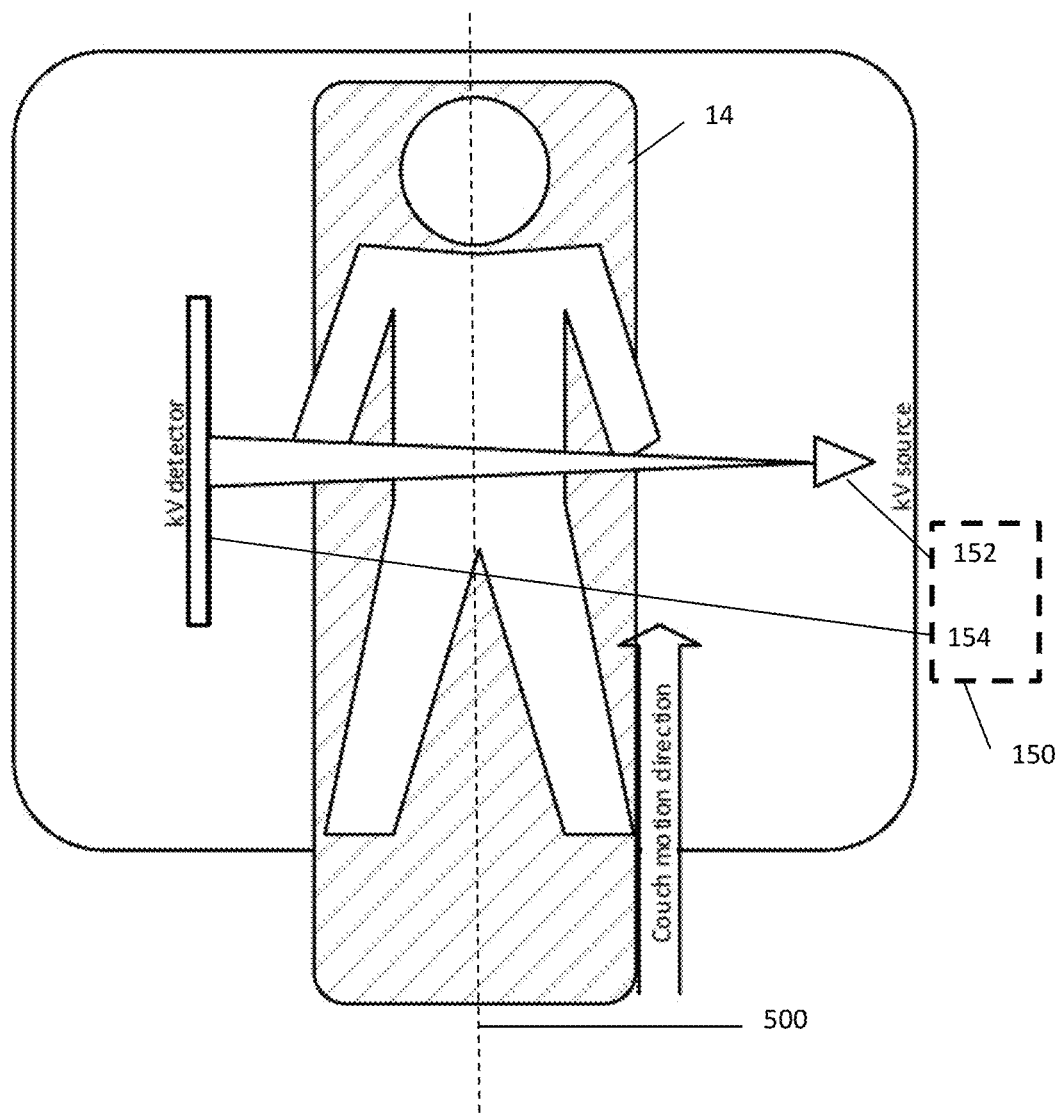
FIG. 5 illustrates an imaging scheme.

FIG. 5 illustrates an imaging scheme. The imaging scheme may be implemented using the image acquisition apparatus 400. As shown in the figure, in one implementation, the patient support 14 is rectilinearly translated while the patient is being supported thereon. The movement of the patient support 14 may be achieved by a positioner that mechanically couples to the patient support 14. The patient support 14 is translated in a direction so that different parts of the patient can be imaged by the imaging device 150 (comprising the imaging source 152 and the imager 154). In the illustrated example, the direction of translation corresponds (e.g., is parallel, or form an angle that is less than 10° with respect) to a longitudinal axis 500 of the patient/the patient support 14. In other examples, the direction of translation may be perpendicular to the longitudinal axis 500, or form other angles (that are different from 0°, 90°, and 180°) with respect to the longitudinal axis 500. Also, in the illustrated example, the imager 154 is at the right side of the patient, which allows the imager 154 to image the patient from the right side. Alternatively, the imager 154 may be placed at the left side of the patient to image the patient from the left side. In addition, in some embodiments, the imager 154 may be placed above the patient to image the patient from the front of the patient. Alternatively, the imager 154 may be placed under the patient to image the patient from the back of the patient. In other embodiments, instead of translating the patient support 14, the imaging device 150 may be rectilinearly translated relative to the patient to image different parts of the patient. In such cases, the movement of the imaging device 150 may be achieved by a positioner that mechanically couples to the imaging device 150. In further embodiments, both the patient support 14 and the imaging device 150 may be moved relative to each other to image different parts of the patient.

In the illustrated example shown in FIG. 5, while the imaging device 150 is at different imaging positions with respect to the patient, the image acquisition apparatus 400 generates control signals to operate the imaging source 152 and the imager 154 to image different parts of the patient 14 along the axis 500 to create a plurality of two-dimensional images. The image acquisition apparatus 400 may then create a composite image based on the two-dimensional images. In one implementation, the two-dimensional images are stitched together to form the composite image.

In some embodiments, the image acquisition apparatus 400 may be configured to operate the imaging device 150 so that it creates two composite images of the patient. For example, the image acquisition apparatus 400 may create a first composite image based on the imaging scheme shown in FIG. 5. The image acquisition apparatus 400 may also operate a positioner to rotate the imaging device 150 to place the imager 154 and the imaging source 152 at another position with respect to the patient. For example, the imager 154 and the imaging source 152 may be rotated about the axis 500 by 90°, so that the imager 154 can image the patient from the front or back of the patient. After the imaging device 150 has been moved, the image acquisition apparatus 400 can then rectilinearly translate the imaging device 150 (imaging source 152 and the detector 154), rectilinearly translate the patient support 14, or both the imaging device 150 and the patient support 14, to generate a second plurality of two-dimensional images. The image acquisition apparatus can then generate the second composite image based on the second plurality of two-dimensional images.

Figure 6:
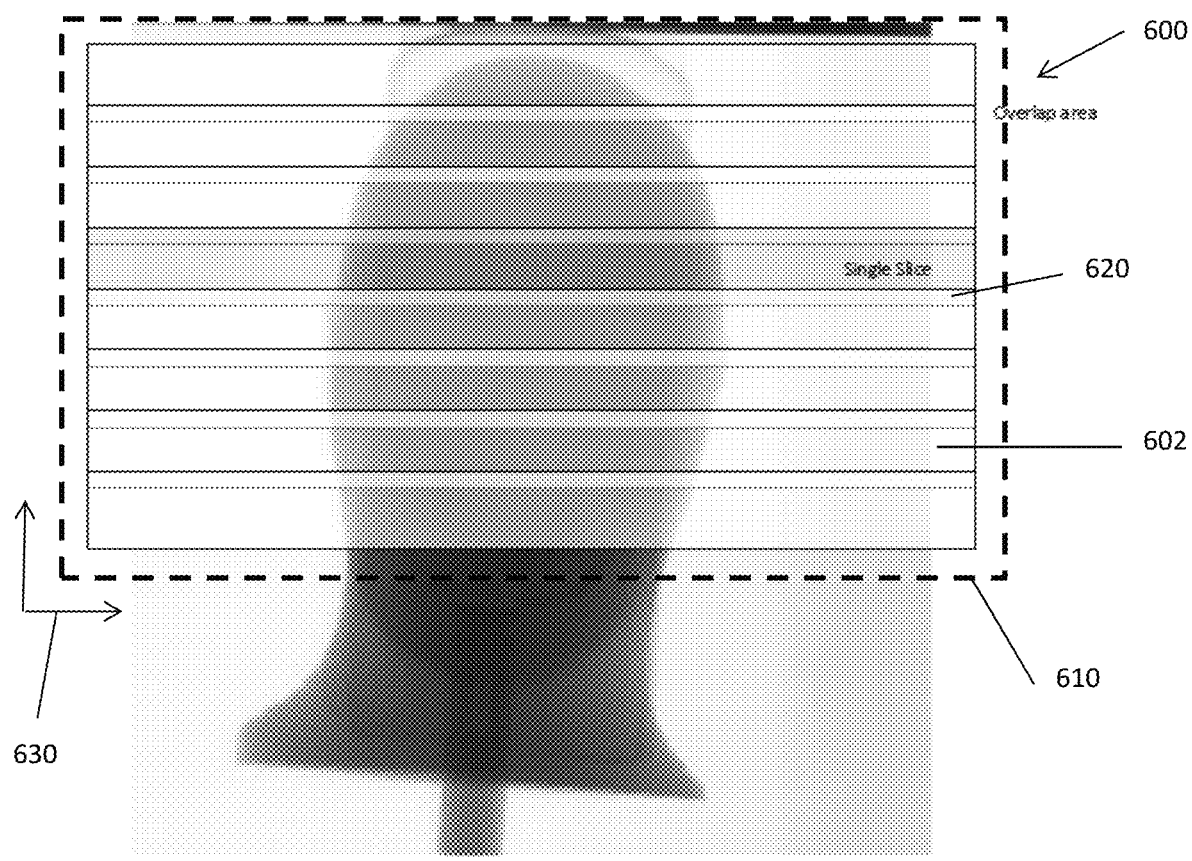
FIG. 6 illustrates a sequence of overlapping two-dimensional images.

The imaging scheme described herein results in a sequence of overlapping images. FIG. 6 illustrates a sequence 600 of overlapping two-dimensional images 602. The two-dimensional images 602 collectively form a composite image 610. The two-dimensional images 602 may be examples of the images 420 discussed with reference to FIG. 4, and the composite image 610 may be an example of the composite image discussed with reference to FIG. 4. As shown in FIG. 6, each of the images 602 has one or more overlapping regions 620 with adjacent image(s). In some embodiments, the image processing unit 430 of the image acquisition apparatus 400 is configured to identify the overlapping region 620 between each adjacent pair of images 602, and align the adjacent pair of images 602 with respect to each other based on the identified overlapping region 620. The aligning of the adjacent images 602 may be accomplished by moving an image 602 in one or more directions within a plane of the image 602 (e.g., along an x-axis and/or along an y-axis). Also, in some embodiments, the image processing unit 430 is configured to stitch adjacent images 602 so that they collectively form the composite image 610. The stitching of the images 602 may involve removing a portion of an image 602 that overlaps with an adjacent image 602. In some cases, the stitching of the images 602 may include blending two overlapping portions of adjacent images 602. Also, in some embodiments, the stitching of the images 602 may be accomplished by arranging (e.g., placing) each image 602 in a coordinate system 630 of the composite image to be formed. The arranging of the image 602 in the coordinate system 630 may be accomplished graphically. Alternatively, or additionally, the arranging of the image 602 in the coordinate system 630 may be accomplished by assigning a position (e.g., X, Y coordinates) for the image 602 with respect to the coordinate system 630. In one implementation, the assigning of the position for the image 602 may be based on an overlapping of the image 602 with adjacent image 602. For example, if a first image 602 is assigned (X1, Y1) in the coordinate system 630 for the composite image 620 to be formed, an adjacent image (e.g., a second image 602) may be assigned coordinate (X2, Y2) in the coordinate system 630, wherein the coordinate (X2, Y2) may be determined based on a region in the second image 602 that overlaps a region in the first image 602. This is performed for each of the images 602 until all of the images 602 is placed in the coordinate system 630 of the composite image 610.

Figure 7:
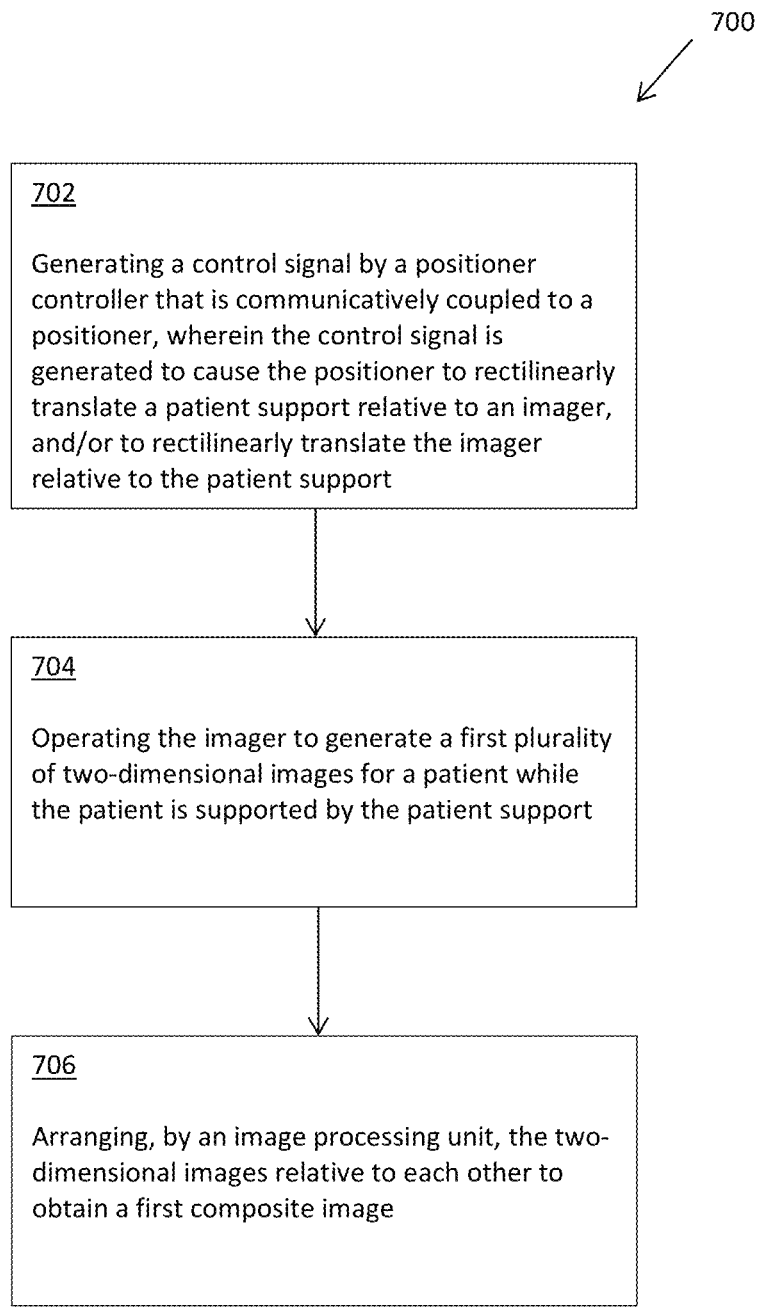
FIG. 7 illustrates an imaging method.

FIG. 7 illustrates an imaging method 700. The imaging method 700 may be performed by the image acquisition apparatus 400 in some embodiments. The imaging method 700 includes: generating a control signal by a positioner controller that is communicatively coupled to a positioner, wherein the control signal is generated to cause the positioner to rectilinearly translate a patient support relative to an imager, and/or to rectilinearly translate the imager relative to the patient support (item 702). The imaging method 700 also includes operating the imager to generate a first plurality of two-dimensional images for a patient while the patient is supported by the patient support (item 704). The imaging method 700 further includes arranging, by an image processing unit, the two-dimensional images relative to each other to obtain a first composite image (item 706).

Optionally, in the method 700, the first composite image is obtained by performing image stitching using the two-dimensional images.

Optionally, the method 700 also includes identifying an overlapping region of at least two of the two-dimensional images.

Optionally, in the method 700, the first composite image covers at least a portion of the patient that is 50 cm or more, 60 cm or more, 70 cm or more, 80 cm or more, 90 cm or more, or 100 cm or more, in length.

Optionally, in the method 700, the imager is operated by an imaging controller to generate a second plurality of two-dimensional images for the patient; and wherein the image processing unit is configured to obtain the second plurality of two-dimensional images and arrange the two-dimensional images in the second plurality of two-dimensional images relative to each other to obtain a second composite image.

Optionally, in the method 700, the first composite image comprises a left or right side view of the patient, and wherein the second composite image comprises a top or bottom view of the patient.

Optionally, the method 700 further includes comparing, by an image comparator, at least a part of the first composite image with at least a part of a reference image to align the at least a part of the first composite image with the at least a part of the reference image. The image comparator may be a part of the image processing unit 430, or alternatively, may be a separate unit from the image processing unit 430.

Optionally, in the method 700, the patient support is moved by the positioner controller based on an alignment between the at least a part of the first composite image and the at least a part of the reference image.

Optionally, in the method 700, the imager is operated by an imaging controller to generate the first plurality of two-dimensional images within 20 seconds or less.

Optionally, in the method 700, the two-dimensional images that are generated within 20 seconds or less collectively cover a length of the patient that is at least 50 cm or more, 60 cm or more, 70 cm or more, 80 cm or more, 90 cm or more, or 100 cm or more.

Optionally, in the method 700, the first plurality of two-dimensional images comprises at least 50 images, at least 60 images, at least 70 images, at least 80 images, at least 90 images, at least 100 images, or more.

Optionally, in the method 700, the imager is operated by an imaging controller to generate the first plurality of two-dimensional images at 10 frames per second or higher, 20 frames/sec or higher, 30 frames/sec or higher, or 40 frames/sec or higher.

Optionally, in the method 700, the image acquisition apparatus is communicatively coupled to an image energy source, wherein the image energy source is coupled to a treatment machine in a half-fan configuration, and wherein the patient support is located off-isocenter with respect to the treatment machine.

Optionally, in the method 700, the first plurality of two-dimensional images is obtained at a same isocenter position associated with a treatment machine.

Optionally, in the method 700, the control signal is generated by the positioner controller to cause the positioner to translate the patient support at a rate that is at least 80% of its maximum speed.

Optionally, in the method 700, the image acquisition apparatus includes a CT image processor, and the method 700 further includes constructing a volumetric image by the CT image processor based on the first composite image.

Optionally, the method 700 further includes generating a volumetric image (e.g., tomosynthesis image/CT image) by the image processing unit based on the first plurality of two-dimensional images.

Optionally, the method 700 further includes controlling a radiation source by an imaging controller to deliver radiation continuously for at least 2 seconds, at least 4 seconds, at least 5 seconds, or at least 6 seconds.

Optionally, the method 700 further includes controlling a radiation source to deliver radiation in pulses.

Optionally, in the method 700, the arranging of the two-dimensional images comprises obtaining couch positions for the patient support or imager positions for the imager, and utilizing the couch positions and/or the imager positions to arrange the two-dimensional images with respect to a reference coordinate for the composite image.

Optionally, in the method 700, the arranging of the two-dimensional images comprises obtaining meta data for the respective two-dimensional images, and utilizing the meta data to map the two-dimensional images to a reference coordinate for the composite image.

Figure 8:
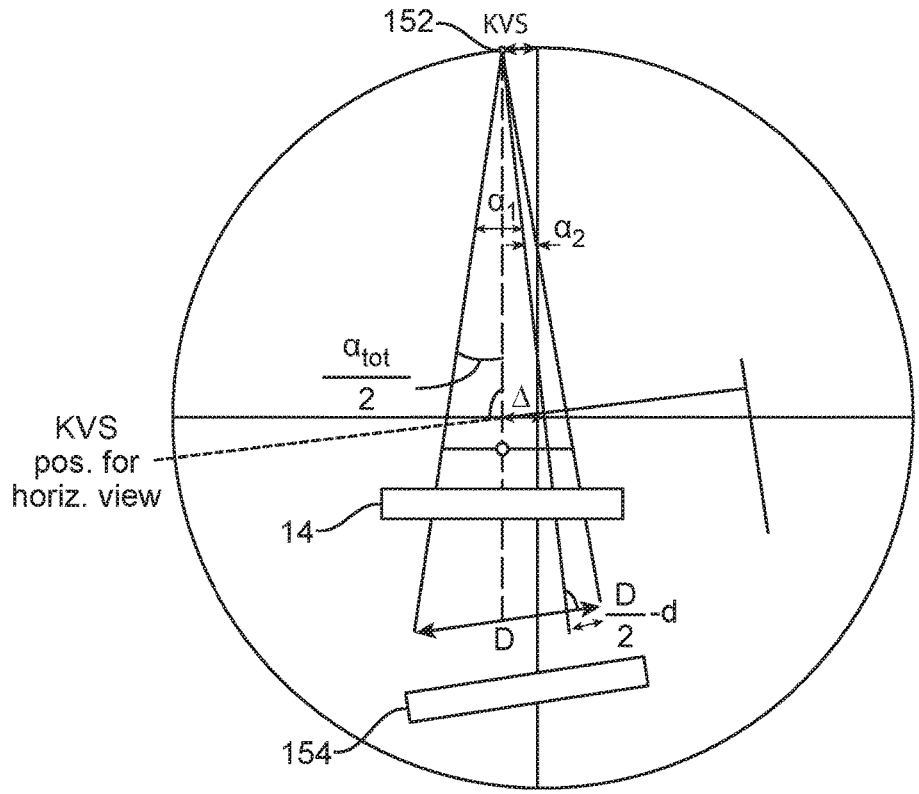
FIG. 8 illustrates an imaging device in a half-fan configuration.

In some embodiments, the patient support 14 may be positioned to align the patient with the isocenter of the treatment system 10 while the image acquisition apparatus 400 operates the imaging device 150 to image the patient. For example, the patient may be laterally aligned with respect to the isocenter axis, such that a center or a reference location of the patient is laterally centered with respect to the isocenter axis (while the patient may be translated along the isocenter axis). In other embodiments, the patient support may be positioned to align the patient off-isocenter with respect to the treatment system 10. This configuration may be desirable when the imaging device 150 is not vertically aligned (e.g., is in a half-fan configuration) with the isocenter of the treatment system 10. FIG. 8 illustrates the imaging source 152 of the imaging device 150 in a half-fan configuration. When in the half-fan configuration, the imaging source 152 is configured to provide a beam with a fan angle that is approximately half (e.g., 0.5±0.1) of the full-fan angle. Imaging devices in half-fan configuration and imaging techniques using half-fan geometry are well known in the art, and therefore will not be described in further detail. As shown in the figure, the patient support 14 is located off-isocenter with respect to the treatment system 10. In such cases, different patient support positions may be used when acquiring top/bottom and side composite images 440 of the patient. For example, the patient support 14, the imaging source 152, and the imager 154 may be positioned as that shown in the figure when the imager 154 images the patient from underneath the patient support 14. The imaging source 152 and the imager 154 may then be rotated about 90° (e.g., 90° plus or minus 15°) to image the patient from a side of the patient. The patient support 14 may then be moved to a different position to allow the imager 154 to image the patient from the side of the patient. Moving the patient support 14 to different positions for acquiring top/bottom and side scans is advantageous because it allows optimization of field of view of each projection (e.g., by moving the patient support 14 as close as possible towards the imager 154 for a larger field of view). In other embodiments, the top/bottom and side scans may be performed with the same lateral and vertical positions for the patient support 14. This has the advantage of reducing or minimizing total image acquisition time and movement of the patient support 14. In addition, in some embodiments, to improve patient positioning and to have a central position of the top/bottom and side images represent a vertical and horizontal projection of the patient center (as in AP and LAT views of CT scout scans), the gantry angle may be offset to compensate for the imager's 154 lateral offset in the half-fan configuration.

In some embodiments, the gantry angle may be selected such that the total viewing angle (defined to be $Alpha_1 + Alpha_2 = Alpha_T$ in FIG. 8) is evenly distributed to both sides of vertical. In the example of the geometry shown in the figure, the positioning parameters may be based on the following relationships:

$$Alpha_2 + Beta = Alpha_1 - Beta \quad \text{(Eq. 1)}$$

$$\text{Thus, } Beta = (Alpha_1 - Alpha_2)/2 \quad \text{(Eq. 2)}$$

$$Alpha_T = Arctan((D/2 + d)/SID) + Arctan((D/2 - d)/SID) \quad \text{(Eq. 3)}$$

$$D = SAD * \sin(Beta) \quad \text{(Eq. 4)}$$

As an example, for imager with D=430 mm, d=175 mm, and SID=154 mm, then $Alpha_T$ may be calculated as 15.7° based on Eq. 3. Also, Beta may be determined as 6.36°, and Delta is calculated as 11.08 cm based on Eq. 4. This Delta represents the amount of lateral offset to "move" the isocenter to place it below the imaging source 152. In some embodiments, the isocenter "shift" direction may be based on the below scheme:

| Imaging source position | Required Delta shift | Type of view |
|---|---|---|
| Top | to the left | vertical view |
| Bottom | to the right | vertical view |
| Left | downwards | horizontal view |
| Right | upwards | horizontal view |

Figure 9:
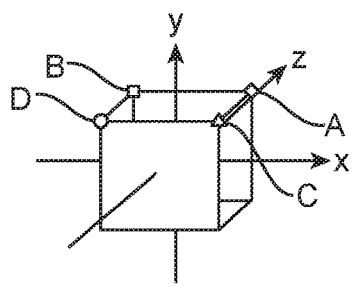
FIG. 9 illustrates different types of projection geometries.
Figure 9:
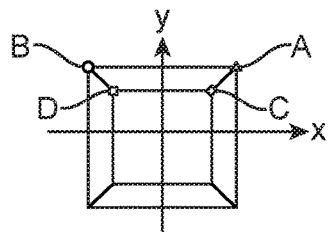
Figure 9:
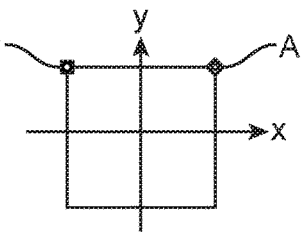
Figure 9:
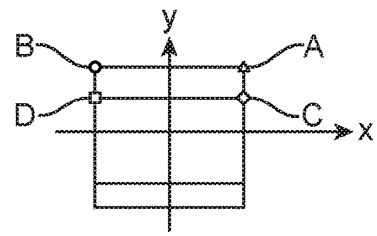

In some embodiments, the two-dimensional images 420 and the composite image 400 created using the technique described herein has different projection properties. For example, in a lateral direction, the image may correspond to a point projection, and in a longitudinal direction, the image may correspond to a parallel projection. FIG. 9 illustrates different types of projection geometries. In some embodiments, if the image has different projection features, processing of the image (e.g., that is involved in 2D/3D matching algorithm, digitally reconstructed radiograph (DRR), etc.) may be implemented in a way that considers such different features.

The image acquisition apparatus 400 and the image acquisition scheme disclosed herein are advantageous because they enable full-body treatment to be performed by the treatment system 10. In some cases, using the technique described herein, two full-length two-dimensional scans may be acquired in the time of a single CBCT, and the required dose for the two two-dimensional scans (for creating the corresponding two composite images) is comparable to the dose required for a regular planar kV image.

The image acquisition scheme described herein is also advantageous over a technique in which targeted treatment area in the patient is split into different treatment plans, which would require image-guided alignment to be performed for each plan. For example, using the "plan-splitting" technique, as much as five separate plans (or more) would have to be created and administered in order to cover a full length of a patient. Such workflow is laborious in planning and execution. In some cases, multiple cone beam computed tomography (CBCT) volumes may be stitched to cover a longer range. However, each volumetric image requires generation of many projection images that result in significant dose delivered to the patient. Also, the generation of projection images for each CBCT image may take a long time (e.g., more than 20 seconds to cover 20 cm in length of the patient). So for 100 cm in length, the image acquisition time can be more than 100 seconds in order for the combined volumetric images to cover the desired length of the patient. Embodiments of the image acquisition technique described herein significantly reduce the image acquisition time, and the amount of imaging dose delivered to patient. For example, in some embodiments, the image acquisition technique described herein may allow imaging of a length of a patient that is more than 100 cm to be completed in less than 12 seconds.

Although the image acquisition apparatus 400 and the imaging acquisition scheme have been described with reference to the treatment system 10, in other embodiments, the image acquisition apparatus 400 and the imaging acquisition scheme may be implemented in other types of treatment system, such as proton treatment system, ultrasound treatment system, etc.

Also, in further embodiments, the image acquisition apparatus 400 and the image acquisition scheme described herein may be implemented in an imaging system (instead of a treatment system). The imaging system may be a CT system, a tomosynthesis system, a radiograph system, an x-ray system, a diagnostic system, a simulator, etc. The image acquisition apparatus 400 may enhance a functionality of such imaging system by operating different components (e.g., imaging source, imager, etc.) of the imaging system to acquire multiple two-dimensional images in accordance with the imaging acquisition scheme described herein. The two-dimensional images may then be stitched to form a composite two-dimensional image (super-2D image) that functions as a scout image, a scanogram, a topogram, etc.

It should be noted that the image acquisition apparatus 400 may not include all of the components 402, 410, 430, 450, 460, 470 in other embodiments. For example, in other embodiments, the image acquisition apparatus 400 may not include the image comparator 460 and/or the volumetric image processor 470. Also, in other embodiments, the non-transitory medium 450 may not be a part of the image acquisition apparatus 400. In such cases, the image acquisition apparatus 400 may be communicatively coupled to the non-transitory medium 450, and may be configured to output information (e.g., two-dimensional images 420, composite image(s) 440, meta data of the images, etc.) for storage at the non-transitory medium 450 and/or for presentation to a user via a display. Furthermore, in some embodiments, two or more of the components 402, 410, 430, 450, 460, 470 of the image acquisition apparatus 400 may be combined. For example, in some embodiments, the positioner controller 402 and/or the imaging controller 410 may be combined into a same module. The image acquisition apparatus 400 (or one or more components therein) may be implemented using hardware, software, or a combination of both.

Specialized Processing System

Figure 10:
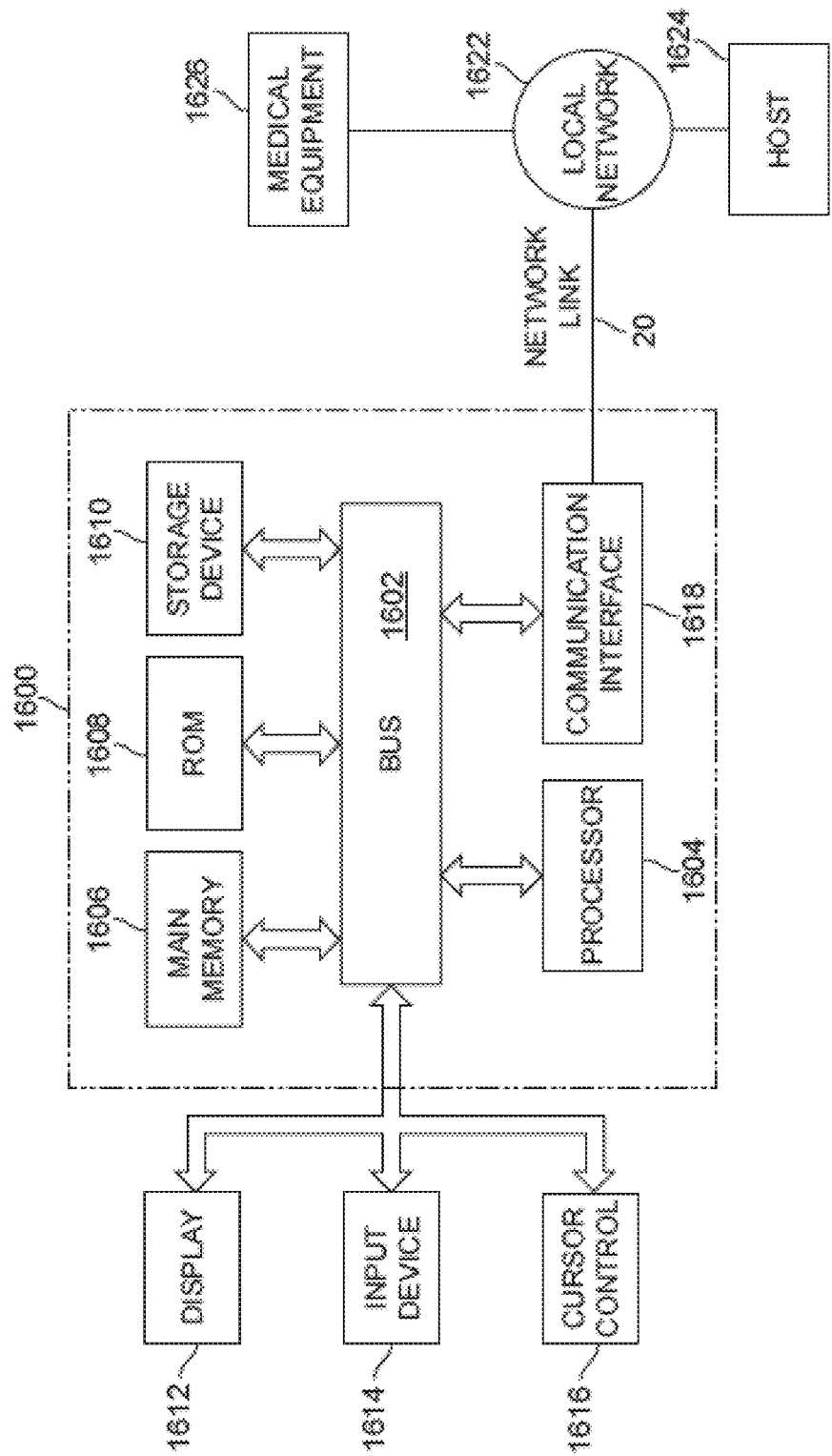
FIG. 10 illustrates a specialized processing system in accordance with some embodiments.

FIG. 10 is a block diagram illustrating an embodiment of a specialized processing system 1600 that can be used to implement various features described herein. For example, in some embodiments, the processing system 1600 may be used to implement the image acquisition apparatus 400, or one or more of its components. Also, in some embodiments, the processing system 1600 may be used to implement the processing unit 54 of FIG. 1. The processing system 1600 may also be used to implement a control that controls an operation of the imager 200, and/or a control that controls an operation of the treatment machine.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk, solid state disk, or optical disk, is provided and coupled to the bus 1602 for storing information and instructions.

The processor system 1600 may be coupled via the bus 1602 to a display 167, such as a flat screen monitor, for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical, solid state or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a flexible disk, hard disk, magnetic tape, or any other magnetic medium, a CD-ROM, any other optical medium, any other physical medium with patterns of holes, a RAM, a PROM, and EPROM, a FLASH-EPROM, solid state disks any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk or solid state disk of a remote computer. The remote computer can load the instructions into its dynamic memory and send the instructions over a network, such as the Internet. The processing system 1600 can receive the data on a network line. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source and/or an imaging device or a switch operatively coupled to a radiation beam source and/or an imaging device. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

As used in this specification, terms such as "first", "second", etc., are used to identify different items, and do not necessarily refer to the order of items. For example, "first composite image" and "second composite image" refer to two different composite images (not that the "first composite image" is first in order, etc.).

Also, as used in this specification, the term "image" may refer to a displayed image and/or to an image that is in electronic form that is not displayed. Similarly, action(s) performed on such image, such as stitching, arranging, moving, etc., may be carried out graphically and/or electronically. For example, a stitching of two images may be performed and/or accomplished by assigning two respective positions for the two images in a coordinate system (wherein when the two images are placed at the two assigned positions, the two images will be combined so that their overlapping regions are aligned).

Exemplary imaging acquisition apparatuses and methods are set out in the following items:

An image acquisition apparatus includes: a positioner controller communicatively coupled to a positioner, wherein the positioner controller is configured to generate a control signal to cause the positioner to rectilinearly translate a patient support relative to an imager, and/or to rectilinearly translate the imager relative to the patient support; an imaging controller configured to operate the imager to generate a first plurality of two-dimensional images for a patient while the patient is supported by the patient support, and while the positioner rectilinearly translates the patient support and/or the imager; and an image processing unit configured to obtain the first plurality of two-dimensional images and arrange the two-dimensional images relative to each other to obtain a first composite image.

Optionally, the image processing unit is configured to obtain the first composite image by performing image stitching using the two-dimensional images.

Optionally, the image processing unit is configured to identify an overlapping region of at least two of the two-dimensional images.

Optionally, the first composite image covers at least a portion of the patient that is at least 100 cm in length.

Optionally, the imaging controller is also configured to operate the imager to generate a second plurality of two-dimensional images for the patient; and wherein the image processing unit is configured to obtain the second plurality of two-dimensional images and arrange the two-dimensional images in the second plurality of two-dimensional images relative to each other to obtain a second composite image.

Optionally, the first composite image comprises a left or right side view of the patient, and wherein the second composite image comprises a top or bottom view of the patient.

Optionally, wherein the image acquisition apparatus further includes an image comparator configured to compare at least a part of the first composite image with at least a part of a reference image to align the at least a part of the first composite image with the at least a part of the reference image.

Optionally, the positioner controller is configured to move the patient support based on an alignment between the at least a part of the first composite image and the at least a part of the reference image.

Optionally, the imaging controller is configured to operate the imager to generate the first plurality of two-dimensional images within 20 seconds or less.

Optionally, the two-dimensional images that are generated within 20 seconds or less collectively cover a length of the patient that is at least 100 cm.

Optionally, the first plurality of two-dimensional images comprises at least 50 images.

Optionally, the imaging controller is configured to operate the imager to generate the first plurality of two-dimensional images at 10 frames per second or higher.

Optionally, the image acquisition apparatus is communicatively coupled to an image energy source, wherein the image energy source is coupled in a half-fan configuration with respect to a treatment machine, and wherein the patient support is located off-isocenter with respect to the treatment machine.

Optionally, the first plurality of two-dimensional images is obtained at a same isocenter position associated with a treatment machine.

Optionally, the positioner controller is configured to generate the control signal to cause the positioner to translate the patient support at a rate that is at least 80% of its maximum speed.

Optionally, the image acquisition apparatus further includes a CT image processor configured to construct a volumetric image based on the first composite image.

Optionally, the image processing unit is also configured to obtain a volumetric image based on the first plurality of two-dimensional images.

Optionally, the imaging controller is also configured to control a radiation source to deliver radiation continuously for at least 2 seconds.

Optionally, the imaging controller is also configured to control a radiation source to deliver radiation in pulses.

Optionally, the image processing unit is configured to obtain couch positions for the patient support or imager positions for the imager, and utilize the couch positions and/or the imager positions to arrange the two-dimensional images with respect to a reference coordinate for the composite image.

Optionally, the image processing unit is also configured to obtain meta data for the respective two-dimensional images, and utilize the meta data to map the two-dimensional images to a reference coordinate for the composite image.

An imaging method performed by an image acquisition apparatus, includes: generating a control signal by a positioner controller that is communicatively coupled to a positioner, wherein the control signal is generated to cause the positioner to rectilinearly translate a patient support relative to an imager, and/or to rectilinearly translate the imager relative to the patient support; operating the imager to generate a first plurality of two-dimensional images for a patient while the patient is supported by the patient support, and while the positioner rectilinearly translates the patient support and/or the imager; and arranging, by an image processing unit, the two-dimensional images relative to each other to obtain a first composite image.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An image acquisition apparatus comprising:
a positioner controller communicatively coupled to a positioner, wherein the positioner controller is configured to generate a control signal to cause the positioner to rectilinearly translate a patient support relative to an imager, and/or to rectilinearly translate the imager relative to the patient support;
an imager comprising a gate control circuit, wherein the gate control circuit is configured to collect image signals from two or more lines of imager elements simultaneously;
an imaging controller configured to operate the imager to generate a first plurality of two-dimensional images for a patient while the patient is supported in a horizontal position by the patient support, the first plurality of two-dimensional images comprising three or more images generated from the image signals and having respective centers aligned along a rectilinear path; and
an image processing unit configured to obtain the first plurality of two-dimensional images and arrange the two-dimensional images relative to each other to obtain a first composite image and compare the first composite image to a reference image generated prior to the first composite image to determine a desired positioning of the patient for a treatment.

2. The image acquisition apparatus of claim 1, wherein the image processing unit is configured to obtain the first composite image by performing image stitching using the two-dimensional images.

3. The image acquisition apparatus of claim 1, wherein the image processing unit is configured to identify an overlapping region of at least two of the two-dimensional images.

4. The image acquisition apparatus of claim 1, wherein the first composite image covers at least a portion of the patient that is at least 100 cm in length.

5. The image acquisition apparatus of claim 1, wherein the imaging controller is also configured to operate the imager to generate a second plurality of two-dimensional images for the patient; and
wherein the image processing unit is configured to obtain the second plurality of two-dimensional images and arrange the two-dimensional images in the second plurality of two-dimensional images relative to each other to obtain a second composite image.

6. The image acquisition apparatus of claim 5, wherein the first composite image comprises a left or right side view of the patient, and wherein the second composite image comprises a top or bottom view of the patient.

7. The image acquisition apparatus of claim 1, wherein the imaging controller is configured to operate the imager to generate the first plurality of two-dimensional images at 10 frames per second or higher.

8. The image acquisition apparatus of claim 1, wherein the image acquisition apparatus is communicatively coupled to an image energy source, wherein the image energy source is coupled in a half-fan configuration with respect to a treatment machine, and wherein the patient support is located off-isocenter with respect to the treatment machine.

9. The image acquisition apparatus of claim 1, wherein the first plurality of two-dimensional images is obtained at a same isocenter position associated with a treatment machine.

10. The image acquisition apparatus of claim 1, further comprising a CT image processor configured to construct a volumetric image based on the first composite image.

11. The image acquisition apparatus of claim 1, wherein the image processing unit is also configured to obtain a volumetric image based on the first plurality of two-dimensional images.

12. The image acquisition apparatus of claim 1, wherein the imaging controller is also configured to control a radiation source to deliver radiation continuously for at least 2 seconds.

13. The image acquisition apparatus of claim 1, wherein the imaging controller is also configured to control a radiation source to deliver radiation in pulses.

14. The image acquisition apparatus of claim 1, wherein the image processing unit is configured to obtain couch positions for the patient support or imager positions for the imager, and utilize the couch positions and/or the imager positions to arrange the two-dimensional images with respect to a reference coordinate for the composite image.

15. The image acquisition apparatus of claim 1, wherein the image processing unit is also configured to obtain meta data for the respective two-dimensional images, and utilize the meta data to map the two-dimensional images to a reference coordinate for the composite image.

16. The image acquisition apparatus of claim 1, wherein the imager has a first dimension measured in a first direction that is perpendicular to the rectilinear path, wherein the first dimension of the imager is sufficient to cover all anatomical features of interest along the rectilinear path, to thereby obviate a need to move the imager in the first direction as the imager is positioned along the rectilinear path.

17. The image acquisition apparatus of claim 1, wherein the imaging controller is configured to operate the imager to generate the three or more images while the positioner rectilinearly translates the patient support and/or the imager along the rectilinear path.

18. An image acquisition apparatus comprising:
a positioner controller communicatively coupled to a positioner, wherein the positioner controller is configured to generate a control signal to cause the positioner to rectilinearly translate a patient support relative to an imager, and/or to rectilinearly translate the imager relative to the patient support;
an imager comprising a gate control circuit, wherein the gate control circuit is configured to collect image signals from two or more lines of imager elements simultaneously;
an imaging controller configured to operate the imager to generate a first plurality of two-dimensional images for a patient while the patient is supported by the patient support the first plurality of two-dimensional images comprising three or more images generated from the image signals and having respective centers aligned along a rectilinear path;
an image processing unit configured to obtain the first plurality of two-dimensional images and arrange the two-dimensional images relative to each other to obtain a first composite image; and
an image comparator configured to compare at least a part of the first composite image with at least a part of a reference image to align the at least a part of the first composite image with the at least a part of the reference image to determine a desired positioning of the patient for a treatment.

19. The image acquisition apparatus of claim 18, wherein the positioner controller is configured to move the patient support relative to a treatment system based on an alignment between the at least a part of the first composite image and the at least a part of the reference image.

20. The image acquisition apparatus of claim 18, wherein the imaging controller is configured to operate the imager to generate the three or more images while the positioner rectilinearly translates the patient support and/or the imager along the rectilinear path.

21. The image acquisition apparatus of claim 18, wherein the reference image comprises at least a part of a CT image generated during treatment planning.

22. An image acquisition apparatus comprising:
a positioner controller communicatively coupled to a positioner, wherein the positioner controller is configured to generate a control signal to cause the positioner to rectilinearly translate a patient support relative to an imager, and/or to rectilinearly translate the imager relative to the patient support;
an imager comprising a gate control circuit, wherein the gate control circuit is configured to collect image signals from two or more lines of imager elements simultaneously;
an imaging controller configured to operate the imager to generate a first plurality of two-dimensional images for a patient while the patient is supported by the patient support, the first plurality of two-dimensional images comprising three or more images generated from the image signals and having respective centers aligned along a rectilinear path; and
an image processing unit configured to obtain the first plurality of two-dimensional images and arrange the two-dimensional images relative to each other to obtain a first composite image and compare the first composite image to a reference image generated prior to the first composite image to determine a desired positioning of the patient for a treatment;
wherein the imaging controller is configured to operate the imager to generate the first plurality of two-dimensional images within 20 seconds or less.

23. The image acquisition apparatus of claim 22, wherein the two-dimensional images that are generated within 20 seconds or less collectively cover a length of the patient that is at least 100 cm.

24. The image acquisition apparatus of claim 23, wherein the first plurality of two-dimensional images comprises at least 50 images.

25. The image acquisition apparatus of claim 22, wherein the imaging controller is configured to operate the imager to generate the three or more images while the positioner rectilinearly translates the patient support and/or the imager along the rectilinear path.

26. An image acquisition apparatus comprising:
a positioner controller communicatively coupled to a positioner, wherein the positioner controller is configured to generate a control signal to cause the positioner to rectilinearly translate a patient support relative to an imager, and/or to rectilinearly translate the imager relative to the patient support;
an imager comprising a gate control circuit, wherein the gate control circuit is configured to collect image signals from two or more lines of imager elements simultaneously;

an imaging controller configured to operate the imager to generate a first plurality of two-dimensional images for a patient while the patient is supported by the patient support, the first plurality of two-dimensional images comprising three or more images generated from the image signals and having respective centers aligned along a rectilinear path; and an image processing unit configured to obtain the first plurality of two-dimensional images and arrange the two-dimensional images relative to each other to obtain a first composite image and compare the first composite image to a reference image generated prior to the first composite image to determine a desired positioning of the patient for a treatment;

wherein the positioner controller is configured to generate the control signal to cause the positioner to translate the patient support at a rate that is at least 80% of its maximum speed.

27. The image acquisition apparatus of claim 26, wherein the imaging controller is configured to operate the imager to generate the three or more images while the positioner rectilinearly translates the patient support and/or the imager along the rectilinear path.

28. An imaging method performed by an image acquisition apparatus, comprising:

generating a control signal by a positioner controller that is communicatively coupled to a positioner, wherein the control signal is generated to cause the positioner to rectilinearly translate a patient support relative to an imager, and/or to rectilinearly translate the imager relative to the patient support;

operating the imager to generate a first plurality of two-dimensional images for a patient while the patient is supported in a horizontal position by the patient support, the first plurality of two-dimensional images comprising three or more images and having respective centers aligned along a rectilinear path, the imager comprising a gate control circuit, wherein the gate control circuit is configured to collect image signals from two or more lines of imager elements simultaneously to generate the three or more images;

arranging, by an image processing unit, the two-dimensional images relative to each other to obtain a first composite image; and comparing, by the image processing unit, the first composite image to a reference image generated prior to the first composite image to determine a desired positioning of the patient for a treatment.

29. The method of claim 28, wherein the imager is operated to generate the three or more images while the positioner rectilinearly translates the patient support and/or the imager along the rectilinear path.

* * * * *